United States Patent

Kesling et al.

Patent Number: 5,782,631
Date of Patent: Jul. 21, 1998

[54] ORTHODONTIC APPLIANCE

[76] Inventors: Christopher K. Kesling, 22 Green Acres, Laporte, Ind. 46350; Robert A. Miller, 2992 Cove Trace, Charlottesville, Va. 22911

[21] Appl. No.: 763,129

[22] Filed: Dec. 11, 1996

[51] Int. Cl.$^6$ .................................................. A61C 3/00
[52] U.S. Cl. .............................. 433/14; 433/11; 433/15
[58] Field of Search ............................. 433/8, 9, 10, 11, 433/12, 13, 14, 15, 16

[56] References Cited

U.S. PATENT DOCUMENTS

| | | | |
|---|---|---|---|
| D. 346,860 | 5/1994 | Kesling | D24/180 |
| 2,062,395 | 12/1936 | Brusse et al. | 433/23 |
| 2,230,315 | 2/1941 | Winslow | 433/11 |
| 2,527,526 | 10/1950 | Brusse | 433/15 |
| 3,052,027 | 9/1962 | Wallshein | 433/9 |
| 3,453,734 | 7/1969 | Rubin | 433/22 |
| 3,508,332 | 4/1970 | Armstrong | 433/21 |
| 3,657,817 | 4/1972 | Kesling | 433/14 |
| 3,893,241 | 7/1975 | Moriarty | 433/22 |
| 3,905,111 | 9/1975 | Kesling | 433/8 |
| 3,913,228 | 10/1975 | Wallshein | 433/18 |
| 3,985,282 | 10/1976 | Miller et al. | 228/175 |
| 4,083,113 | 4/1978 | Millet et al. | 432/17 |
| 4,144,642 | 3/1979 | Wallshein | 433/11 |
| 4,350,487 | 9/1982 | Kesling et al. | 433/14 |
| 4,427,381 | 1/1984 | Hall | 433/14 |
| 4,551,094 | 11/1985 | Kesling | 433/8 |
| 4,664,626 | 5/1987 | Kesling | 433/14 |
| 4,799,882 | 1/1989 | Kesling | 433/8 |
| 4,842,513 | 6/1989 | Haarmann | 433/9 |
| 5,035,614 | 7/1991 | Greenfield | 433/21 |
| 5,057,012 | 10/1991 | Kesling | 433/17 |
| 5,096,416 | 3/1992 | Hulsink | 433/6 |
| 5,098,288 | 3/1992 | Kesling | 433/9 |
| 5,125,832 | 6/1992 | Kesling | 433/8 |
| 5,127,828 | 7/1992 | Suyama | 433/8 |
| 5,154,606 | 10/1992 | Wildman | 433/8 |
| 5,161,969 | 11/1992 | Pospisil et al. | 433/8 |
| 5,232,364 | 8/1993 | Rosen | 433/8 |
| 5,263,859 | 11/1993 | Kesling | 433/9 |
| 5,306,142 | 4/1994 | Richards | 433/22 |
| 5,338,191 | 8/1994 | Hamula | 433/23 |
| 5,470,228 | 11/1995 | Franseen et al. | 433/8 |
| 5,540,586 | 7/1996 | Hanson | 433/22 |

Primary Examiner—John J. Wilson
Attorney, Agent, or Firm—Barnes & Thornburg

[57] ABSTRACT

An orthodontic appliance includes a pin and a bracket. The pin has first and second portions joined by a bight. The first portion of the pin includes a pair of tie wings. The bracket includes a base with a pair of arms extending therefrom terminating in tie wings. A platform is positioned on the base between the arms. A first slot separates the tie wings. A second slot extends generally perpendicularly to the first slot through both arms and the platform. In use, the base of the bracket is attached to a tooth, an archwire is positioned in the first slot and the second portion of the pin is inserted through the second slot, such that the tie wings are adjacent the first slot. A ligature tie is then positioned about the tie wings to hold the archwire in place. In an alternative embodiment, an extension on the pin is bent about a portion of the bracket to secure the bracket to the archwire. The ligature tie is eliminated.

6 Claims, 2 Drawing Sheets

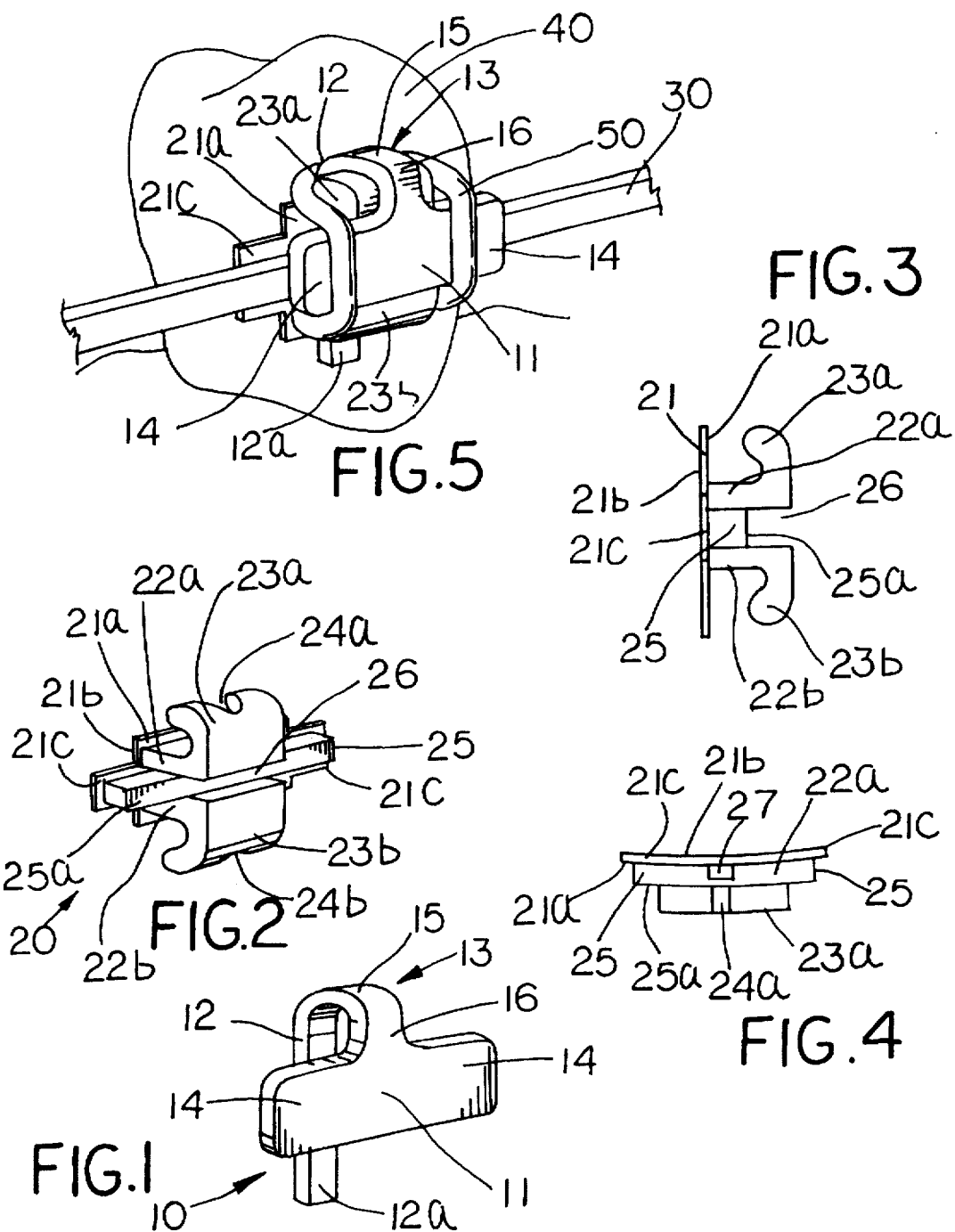

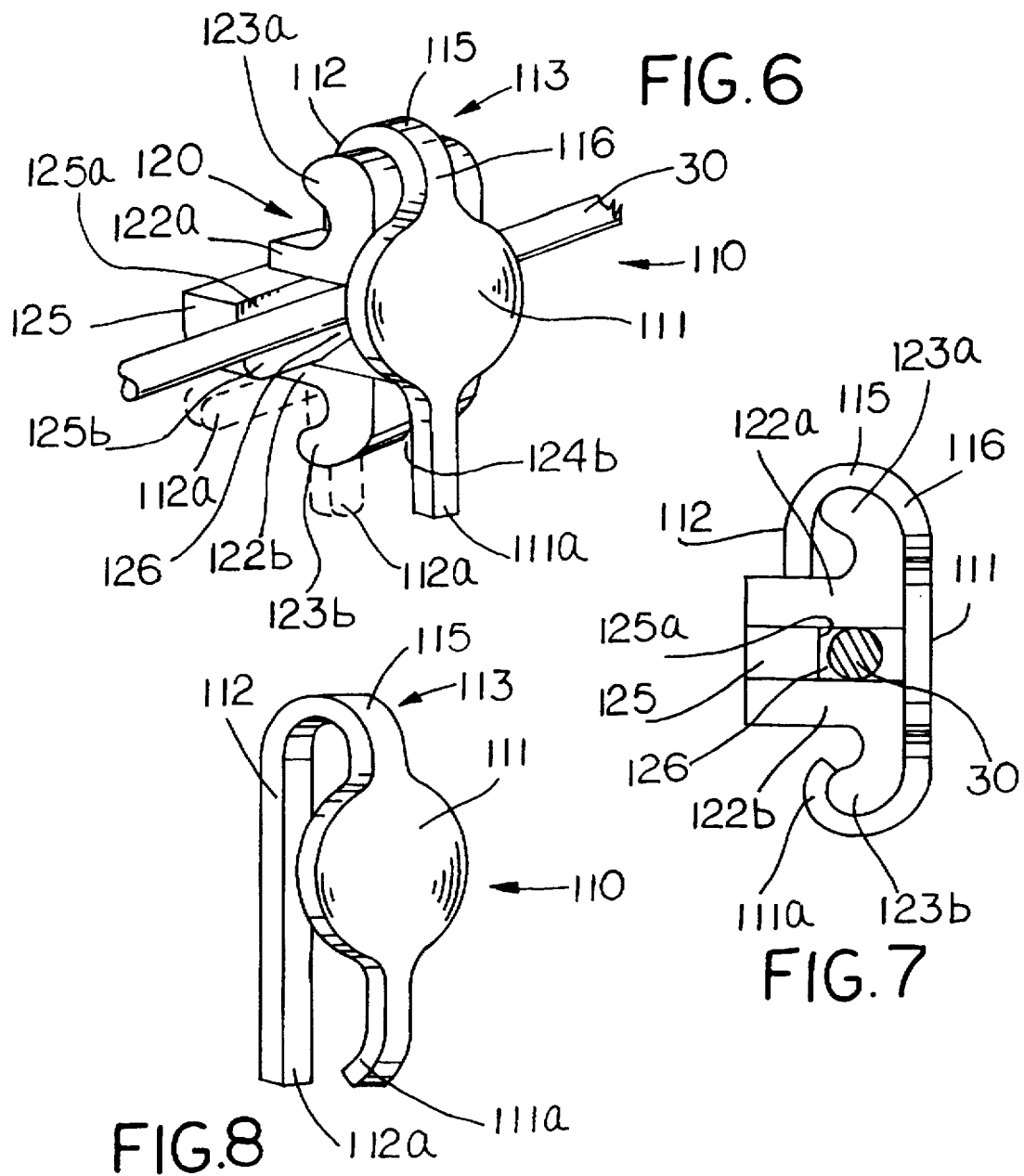

5,782,631

ORTHODONTIC APPLIANCE

BACKGROUND AND SUMMARY OF THE INVENTION

The present invention relates to orthodontic appliances and, in particular, to an orthodontic bracket and ligation pin.

Orthodontic appliances, commonly known as braces, are widely used to reposition teeth for better functioning or for cosmetic reasons. Braces typically include a bracket secured to the tooth and connected to a wire known as an archwire. The archwire is placed under tension, which is transmitted to the teeth through the brackets, causing the teeth to move.

The archwire is typically secured to the bracket by a ligature tie. A typical ligature tie consist of a small, ring-shaped elastic member or a steel wire. The ligature tie may be used to secure the archwire by positioning the archwire in a groove or slot in the bracket and wrapping the ligature tie around a portion of the bracket to hold the archwire within the slot. Examples of such arrangements are shown in U.S. Pat. No. 5,540,586 and U.S. Pat. No. 5,470,228.

When repositioning teeth with braces, it is often necessary to cause the tooth and bracket to slide along the archwire. In some of the prior art devices, the ligature tie comes in direct contact with the archwire. This contact results in friction between the ligature tie and archwire, thereby making it more difficult to slide the bracket and tooth along the archwire. Thus, it may be desirable to reduce the friction between the archwire and the ligature tie, thereby making it easier to slide the tooth and bracket along the archwire.

Accordingly, it is an object of the present invention to provide an orthodontic appliance.

Another object of the present invention is to provide an orthodontic appliance that reduces friction between the ligature tie and archwire.

Yet another object of the present invention is to provide an orthodontic appliance that allows for easier movement of the tooth and bracket along the archwire.

These and other objects of the present invention are obtained by an orthodontic appliance having a pin and a bracket. The pin has a first portion and a second portion. The first portion may be curved. The bracket has a base, a first labially facing slot for receiving an archwire and a second vertical slot for receiving the second portion of the pin. The first portion of the pin covers a portion of the first slot. A pair of arms extends from the base and a tie wing is connected to each arm. The slots are generally perpendicular to one another. The first portion of the pin includes a pair of tie wings. The second portion of the pin is located behind the archwire when the archwire is disposed in the first slot and the second portion of the pin is disposed in the second slot. The second portion may extend completely through the second slot and may be positioned generally parallel to the archwire.

According to one embodiment of the invention, the first portion of the pin extends in the mesial and distal directions and the second portion of the pin extends in the incisal and gingival directions. The first and second portions may be connected by a bight.

According to another embodiment of the present invention, the pin may include an extension surrounding a portion of the bracket.

According to another embodiment of the present invention, an orthodontic appliance includes a bracket having first and second slots, an archwire located in the first slot, a pin located at least partially within the second slot and an elastomeric ring secured about a portion of the bracket and pin to secure the bracket to the archwire. A portion of the pin may be located between the elastomeric ring and the first slot.

Other objects, advantages and novel features of the present invention will be apparent upon consideration of the following description of the preferred embodiments and accompanying drawings.

BRIEF DESCRIPTION OF THE DRAWINGS

FIG. 1 is a perspective view of an orthodontic pin that is a component of an orthodontic appliance according to the present invention.

FIG. 2 is a perspective view of a bracket that is a component of an orthodontic appliance according to the present invention.

FIG. 3 is a side plan view of the bracket shown in FIG. 2.

FIG. 4 is a top plan view of the bracket shown in FIG. 2.

FIG. 5 is a perspective view of the bracket of FIG. 2 and the ligature pin of FIG. 1 placed on a tooth and secured to an archwire by a ligature tie.

FIG. 6 is a perspective view of another embodiment of the present invention.

FIG. 7 is a side plan view of the embodiment shown in FIG. 6.

FIG. 8 is a perspective view of another embodiment of the pin shown in FIGS. 6 and 7.

DETAILED DESCRIPTION OF THE PREFERRED EMBODIMENTS

FIG. 1 is a perspective view of an orthodontic pin 10 that is a component of an orthodontic appliance according to the present invention. Pin 10 includes a first portion 11 and a second portion 12 having an end 12a, connected by a bight 13. In the embodiment shown, first portion 11 is a generally rectangular member having two ligature tie wings 14. Tie wings 14 curve away from second portion 12 of pin 10. Second portion 12 is a generally elongated member having a substantially rectangular cross-section. Bight 13 includes a first segment 15 that is generally perpendicular to second portion 12 of pin 10 and a second segment 16 that is generally parallel to second portion 12 of pin 10 and generally perpendicular to first segment 16. Pin 10 is preferably made from a stiff, deformable material, such as brass or stainless steel. Alternatively, it can be formed as a resilient member, as described below.

Bracket 20 (FIG. 2) includes a base 21 having a front surface 21a and a rear surface 21b. Base 21 is a generally rectangular member having a pair of extensions 21c extending in the distal and mesial directions. Base 21 may be curved to correspond to the curvature of the teeth. A first arm 22a and a second arm 22b extend from front surface a of base 21. Arms 22a and 22b terminate, respectively, in tie wings 23a and 23b. A notch 24a is formed in tie wing 23a and a notch 24b is formed in tie wing 23b.

Bracket 20 further includes a raised support platform 25 that extends beyond tie wings 23a and 23b onto extensions 21c. Platform 25 is a generally rectangular member that supports an archwire, as described below. Tie wings 23a and 23b are spaced apart so as to form a first labially facing slot 26 therebetween. Front surface 25a of platform 25 forms the back wall of slot 26.

Slot 26 can be better seen in FIG. 3, which is a side plan view of the bracket shown in FIG. 2. FIG. 3 also shows that first arm 22a and second arm 22b are angled upward and that tie wings 23a and 23b curve inward toward base 21. Tie wings 23a and 23b are curved inward toward base 21 to prevent the ligature tie from slipping off when the archwire is secured to bracket 20, as described below.

FIG. 4 is a top plan view of the bracket shown in FIG. 2. In this figure, it can be seen that bracket 20 further includes a second vertical slot 27. Slot 27 runs through first arm 22a, platform 25 and second arm 22a, behind tie wings 23a and 23b. Slot 27 receives second portion 12 of pin 10, as described below. Bracket 20 may be made of metal, ceramic or plastic.

FIG. 5 shows an archwire 30 attached to a tooth 40 by pin 10, bracket 20 and a ligature tie 50. Rear surface 21b of base 21 is cemented to tooth 40 by a known compound. Archwire 30 is then placed within first slot 26 between tie wings 23a and 23b. Second portion 12 of pin 10 is then inserted downwardly through second slot 27 of bracket 20 such that end 12a extends below arm 22b as shown. In this position, first segment 15 of bight 13 rests in notch 24a of tie wing 23a and first portion 11 and tie wings 14 of pin 10 cover first slot 26. A ligature tie 50, preferably in the form of an elastomeric ring, is then positioned behind tie wings 23a and 23b and in contact with second portion 12 of pin 10. In this position, ligature tie 50 is positioned against tie wings 14 of pin 10 on the labial side. Thus, as attached to tooth 40, second portion 12 of pin 10 extends in the gingival and incisal directions. Tie wings 14 extend in the mesial and distal directions. As connected to the tooth, pin 10 and bracket 20 hold ligature tie 50 away from and out of contact with archwire 30, thereby reducing friction forces.

FIG. 6 shows another embodiment of a pin according to the present invention. Features of this embodiment corresponding to the previous embodiment are indicated by the numeral "1" before the remainder of the designation. In this embodiment, pin 110 includes a rounded first portion 111, but no ligature tie wings. An extension 111a is connected to first portion 111 and extends adjacent tie wing 123b. End 112a of second portion 112 of pin 110 does not extend below tie wing 123b. Alternatively, end 112a of second portion 112 can be extended, as shown in dashed lines, below tie wing 123b and bent generally parallel with archwire 30 and platform 125. End 12a of the embodiment of FIG. 5 could also be positioned parallel to archwire 30. Note also that the bracket 120 does not include a base. Also, platform 125 is rounded at its lower corners at 125b.

FIG. 7 shows a side plan view of the embodiment shown in FIG. 6. This view shows extension 111a of pin 110 positioned around tie wing 123b. Alternatively, pin 110 can be made from a resilient material and extension 111a can be pre-bent so as to angle inwardly toward second portion 112, as shown in FIG. 8. When second portion 112 is inserted in slot 127, extension 111a would flex outward as it contacts bracket 120. When second portion 112 is fully inserted, extension 111a will snap inward toward second portion 112 and be positioned about tie wing 123b. In either case, bracket 120 is secured to archwire 30 without use of a ligature tie. The interaction of pin 110 and bracket 120 secures bracket 120 to the tooth. Thus, the friction between the archwire and ligature tie is completely eliminated.

Although the present invention has been described and illustrated in detail, it is to be clearly understood that the same is by way of illustration and example only and is not to be taken by way of limitation. Numerous changes can be made to the embodiments shown without departing from the invention. For example, the pins shown could take various configurations without departing from principles of the invention. Similarly, any one of a number of known brackets could be utilized. Accordingly, the spirit and scope of the invention are to be limited only by the terms of the appended claims.

What is claimed is:

1. An orthodontic appliance, comprising:
 a bracket;
 a first labially facing slot extending through the bracket;
 a second vertical slot extending through the bracket;
 an archwire located in the first slot;
 a pin located at least partially within the second slot; and
 an elastomeric ring secured about a portion of the bracket and pin to secure the bracket to the archwire.

2. The orthodontic appliance according to claim 1, wherein a portion of the pin extends through the second slot and is positioned generally parallel to the first slot.

3. The orthodontic appliance according to claim 1, wherein the pin includes a pair of tie wings about which the elastomeric ring is located.

4. The orthodontic appliance according to claim 3, wherein the tie wings extend in the mesial and distal directions.

5. The orthodontic appliance according to claim 1, wherein the pin includes a first portion, a second portion and a third portion connecting said first and second portions in spaced-apart relationship.

6. The orthodontic appliance according to claim 5, wherein the second portion of the pin is located in the second slot and the first portion of the pin is adjacent the first slot.

* * * * *